(12) United States Patent
Licht et al.

(10) Patent No.: US 6,329,312 B1
(45) Date of Patent: Dec. 11, 2001

(54) METALLOCYCLE METALLOCENES AND THEIR USE

(75) Inventors: Erik Licht; Helmut G. Alt, both of Bayreuth (DE); M. Bruce Welch, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/334,890

(22) Filed: Jun. 17, 1999

Related U.S. Application Data

(60) Provisional application No. 60/090,037, filed on Jun. 19, 1998.

(51) Int. Cl.[7] ................................................ B01J 31/00
(52) U.S. Cl. ................... 502/117; 502/103; 502/150; 502/152; 502/154; 526/160; 526/943
(58) Field of Search .................................... 502/103, 117, 502/150, 152, 154; 526/160, 943

(56) References Cited

U.S. PATENT DOCUMENTS

| | | | |
|---|---|---|---|
| 5,153,157 | 10/1992 | Hlatky et al. | 502/117 |
| 5,238,892 | 8/1993 | Chang | 502/11 |
| 5,241,025 | 8/1993 | Hlatky et al. | 526/129 |
| 5,384,299 | * 1/1995 | Turner et al. | 502/155 |
| 5,453,410 | 9/1995 | Kolthammer et al. | 502/155 |
| 5,498,581 | 3/1996 | Welch et al. | 502/102 |
| 5,654,454 | 8/1997 | Peifer et al. | 556/11 |
| 5,753,785 | 5/1998 | Reddy et al. | 526/75 |
| 5,834,393 | * 11/1998 | Jacobsen et al. | 502/152 |

* cited by examiner

*Primary Examiner*—Elizabeth D. Wood
(74) *Attorney, Agent, or Firm*—Edward L. Bowman

(57) ABSTRACT

Metallocycle metallocenes are produced by reacting a first metallocene having an aralkyl group or an aryl dialkyl silyl group attached to a cyclodienyl group with about two molar equivalents of an alkali metal alkyl having at least 4 carbon atoms. The use of the metallocycle metallocenes as components of catalyst for the polymerization of olefins is also disclosed.

7 Claims, 3 Drawing Sheets

154

152

153

155

157

158

159

160

161

162

164

165

167

169

173a,b 174a,b 175a,b 176a,b 177a,b

187

181

183

180

METALLOCYCLE METALLOCENES AND THEIR USE

This application claims the benefit of U.S. Provisional Application No. 60/090037, filed Jun. 19, 1998, the disclosure of which is incorporated herein by reference.

BACKGROUND OF THE INVENTION

In order for metallocenes to be particularly useful in slurry type polymerization processes, it has generally been found necessary to form a catalyst system in which the metallocene and the cocatalyst are insoluble during the polymerization. Various approaches have been taken to provide insoluble heterogeneous catalyst systems that would be applicable. One technique involves the employment of metallocenes containing unsaturated substituents which can be prepolymerized in the presence of a cocatalyst to produce a solid insoluble catalyst system. An example of such a process is disclosed in U.S. Pat. No. 5,498,581.

Another approach for preparing such an insoluble heterogeneous catalyst system involves the employment of a special type of metallocene referred to as a metallocycle metallocene. A metallocycle type metallocene is one in which one of the cyclic dienyl groups that is pi bonded to the metal of the metallocene also contains a substituent which is also bonded to the metal of the metallocene. An example of such a metallocene is disclosed in U.S. Pat. No. 5,654,454. In that case, the metallocycle was produced by a hydrozirconation type reaction. Such compounds are referred to as metallocycles for the reason that there is what can be viewed as a cyclic structure comprising the cyclic dienyl group pi bonded to the zirconium and the substituent on the cyclic dienyl group being also bonded to the metal. It is believed that such compounds form self supported catalyst systems as a result of repeated ethylene insertions into the metal-substituent bond to result in a prepolymer having pendant metallocene groups.

An object of the present invention is to provide a new catalyst system comprising the product resulting from the combination of a cocatalyst and a metallocycle metallocene produced from a metallocene having an arylalkyl substituent on at least one of the cyclic dienyl groups of the metallocene by reacting the metallocene with two equivalents of an alkali metal alkyl.

Another object of the present invention is to provide a process for producing polymers from olefins comprising contacting an olefin with such a catalyst system under polymerization conditions.

Still another object of the present invention is provide a halogen-free metallocene capable of use as an olefin polymerization catalyst.

SUMMARY OF THE INVENTION

In accordance with the present invention, there is provided a method for producing metallocycle metallocenes which involves reacting a first metallocene having an aralkyl group, an aralkyldialkylsilyl, or an aryl dialkyl silyl group attached to a cyclodienyl group with about two molar equivalents of an alkali metal alkyl having at least 4 carbon atoms. (The term aralkyldialkylsilyl refers to groups of the formula —R'''—Si(R)$_2$— wherein R''' is a alkylene radical having 1 to 2 carbon atoms in the chain between the two free valences of R'''.)

In accordance with the present invention, one can produce metallocenes having the formula

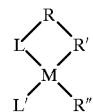

wherein L is a radical having a cyclodienyl skeleton, examples of which would include hydrocarbyl substituted and unsubstituted, cyclopentadienyl, indenyl, fluorenyl, and tetrahydroindenyl,; R' is an aryl group, i.e. a cyclic compound having at least one six membered ring, examples of which would include phenyl, indenyl, fluorenyl, naphthyl, benzoindenyl, anthracenyl, phenanthracenyl, or the like, which could be hydrocarbyl substituted or unsubstituted; R is a divalent alkyl, alkylsilyl, or dialkylsilyl radical wherein the number of atoms separating L and R' is in the range of 1 to 3, L' is a hydrocarbyl substituted and unsubstituted radical having a cyclodienyl skeleton, examples of which would include cyclopentadienyl, indenyl, fluorenyl, and tetrahydroindenyl; R'' is an aliphatic radical having 1 to 10 carbon atoms; and M is a transition metal, preferably Zr, Hf, or Ti. L and L' can optionally be connected to each other by a bridging structure. Examples of such bridging structures include divalent hydrocarbyl structures, preferably having 1 to 10 carbon atoms, such as dimethyl methylene, and dihydrocarbyl silyl structures, preferably having 2 to 10 carbon atoms, such as dimethylsilylene.

In certain cases one can also use the present invention to form metallocenes of the formula

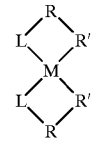

wherein L is a cyclopentadienyl radical, each R is defined as above, and one R' is an indenyl radical and the other is an indanyl radical. Such metallocycles could be referred to as di-metallocycles or as double metallocycles. One specific example would be where each R is dimethylmethylene. Such a dimetallocycle can be produced by reacting bis(1-(n5-cyclopentadienyl)-1,1-dimethyl-1-(1-indenyl)-methane) zirconium dichloride with two equivalents of butyllithium. The resulting double metallocycle could be called (1-(n5-cyclopentadienyl)-1,1-dimethyl-1-indenyl)-methane) zirconium (1-(n5-cyclopentadienyl)-1,1-dimethyl-1-(1-indanyl)-methane), since in one ligand the zirconium is bonded to the cyclopentadienyl through pi bonds and to the indenyl and in the other ligand the zirconium is bonded to the cyclopentadienyl through pi bounds and to the indanyl through a sigma bond, the indanyl having been formed because the hydrogen is not transferred in this case to the butene ligand but rather to the indenyl to form indanyl. Such a compound is illustrated as compound 187 in FIG. 2.

The resulting metallocenes can be used to as catalysts for the polymerization of olefins.

DETAILED DESCRIPTION OF THE INVENTION

Figure 1:
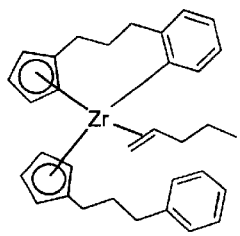
FIGS. 1–3 illustrate various metallocycle metallocenes of the present invention.
Figure 1:
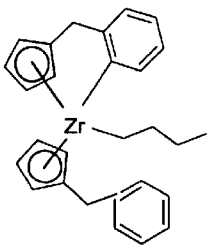
Figure 1:
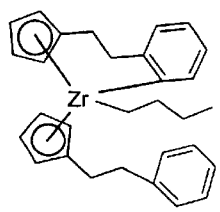
Figure 1:
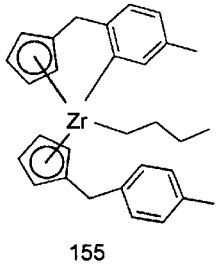
Figure 1:
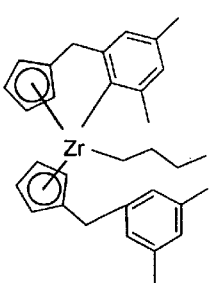
Figure 1:
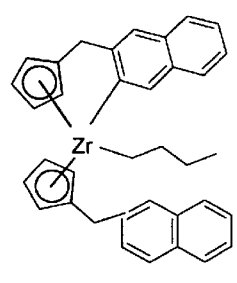
Figure 1:
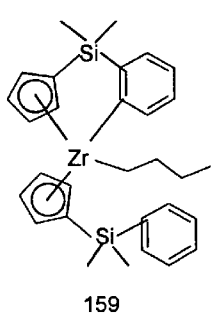
Figure 1:
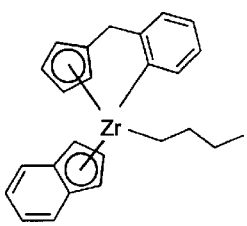
Figure 1:
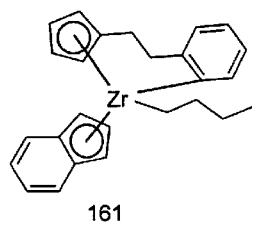
Figure 1:
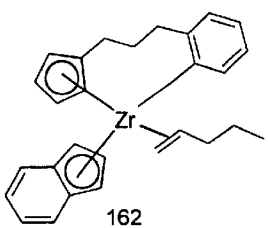
Figure 1:
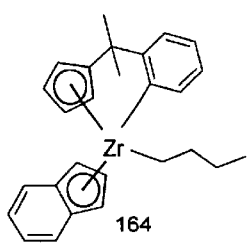
Figure 1:
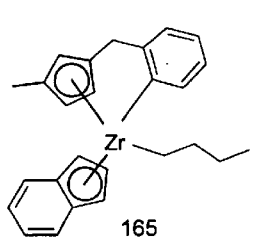

In accordance with the present invention the new metallocenes are prepared by reacting a first metallocene having two halogens attached to the metal and having an aralkyl group, a aralkyldialkylsilyl, or an aryldialkylsilyl group attached to a cyclodienyl group with about two molar equivalents of an alkali metal alkyl, preferably one having at least 4 carbon atoms. Preferably there are 1 to 3 atoms separating the cyclopentadienyl group and the aromatic group.

It is contemplated that the process can be applied to any metallocene in which there is a cyclodienyl group which has the required type of aralkyl, alkyl dialkylsilyl, or aryl dialkyl silyl group. Thus it is contemplated that the process is applicable to both bridged and unbridged sandwich bonded metallocenes and to constrained geometry monocyclodienyl metallocenes such as (3-phenylmethyl cyclopentadienyl)(t-butyl amido)dimethyl silane titanium dichloride. The currently preferred metallocenes are those of the transition metal compounds Ti, Zr, and Hf.

The metallocycle metallocene is produced by reacting a suitable first metallocene having two halogens attached to the metal and having the aralkyl, alkyldialkylsilyl, or aryl-dialkylsilyl substitution with an alkali metal alkyl. Suitable first metallocenes include compounds of the formula

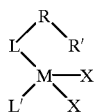

wherein L is a radical having a cyclodienyl skeleton, examples of which would include cyclopentadienyl, indenyl, fluorenyl, and tetrahydroindenyl, hydrocarbyl substituted and unsubstituted; R' is an aryl group, i.e. a cyclic compound having at least one six membered ring, examples of which would include phenyl, indenyl, fluorenyl, naphthyl, benzoindenyl, anthracenyl, phenanthracenyl, or the like, which could be hydrocarbyl substituted or unsubstituted; R is a divalent alkyl, alkyldialkylsilyl, or dialkylsilyl radical wherein the number of atoms separating L and R' is in the range of 1 to 3, L' is a hydrocarbyl substituted and unsubstituted radical having a cyclodienyl skeleton, examples of which would include cyclopentadienyl, indenyl, fluorenyl, and tetrahydroindenyl; each X is a halogen, and M is a transition metal, preferably Zr, Hf, or Ti. L and L' can optionally be connected to each other by a bridging structure. Examples of such bridging structures include divalent hydrocarbyl structures, preferably having 1 to 10 carbon atoms, such as dimethyl methylene, and dihydrocarbyl silyl structures, preferably having 2 to 10 carbon atoms, such as dimethylsilylene. It is within the scope of the invention for L' to be the same as L—R—R'.

Preferably the alkali metal alkyl has 4 to 6 carbon atoms. The reaction of the first metallocene and the alkali metal alkyl can be conducted in any suitable manner. Typically the reaction would be carried out by forming a solution of the metallocene in a hydrocarbon, for example toluene, and then adding a solution of the alkali metal alkyl. The temperature employed can vary widely; however, temperatures below 0° C. are generally preferred for the combining the metallocene and the alkali metal alkyl, for example 0 to −90° C., more typically −20° C. to −80° C.

The type of bond that is formed between the aromatic group R' and the metal M differs depending on the number of atoms in R which separate R' and L.

Figure 2:
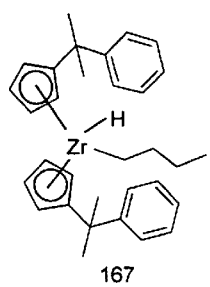
Figure 2:
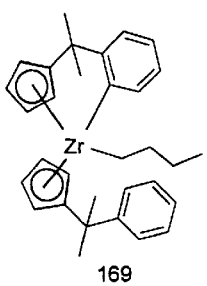
Figure 2:
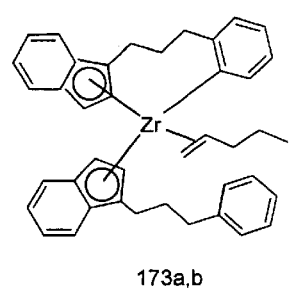
Figure 2:
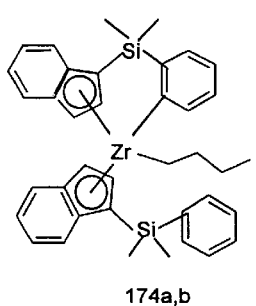
Figure 2:
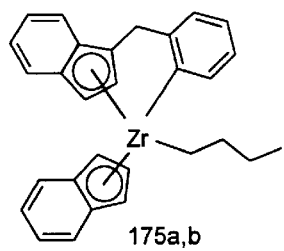
Figure 2:
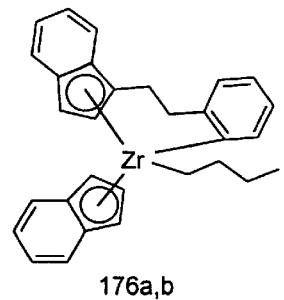
Figure 2:
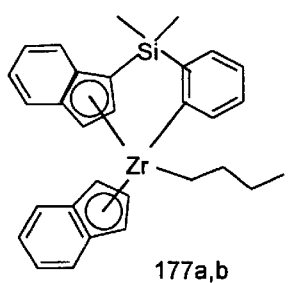
Figure 2:
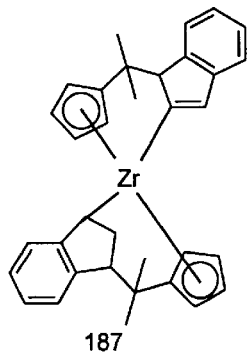
Figure 2:
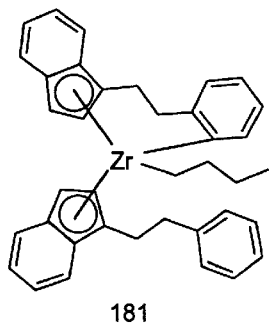
Figure 3:
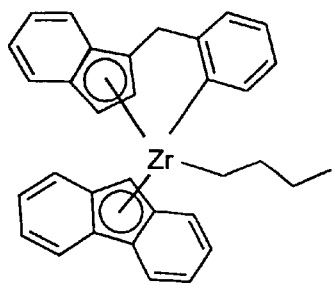
Figure 3:
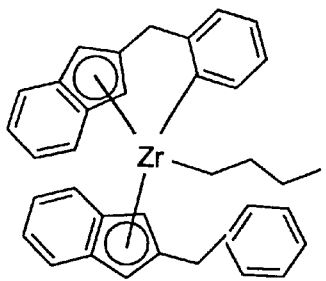

Such a technique has been used to form the metallocycle metallocenes illustrated in FIGS. 1–3.

Various techniques can be used to form metallocenes having the omega alkenyl aryl groups or omega dialkyl silyl aryl groups for use as the starting point for making the inventive metallacyle metallocenes. Typically the metallocenes are prepared by reacting the desired organic compound or compounds with an alkali metal alkyl and a transition metal halide. Compounds suitable for making bridged mettalacycles can be made by reacting fluorenyl lithium or indenyl lithium with 1-(9-fluorenyl)-1-(3-(6,6-dimethylfulvene)-1,1-dimethyl methane. Further lithium fluorenyl can be reacted with 6,6 dimethyl benzofuilvene to produce a lithium intermediate in which fluorenyl and indenyl are connected by dimethylmethylene and then that intermediate reacted with 6,6 dimethylfulvene to produce a compound in which there is a cyclopentadienyl further connected to the indenyl by another dimethylmethylene bridge. Cyclopentadienyl sodium can be reacted with omega-phenyl-1-bromo alkanes or omega-phenyl-1-bromo dialkyl silyl compounds in liquid ammonia to produce cyclopentadienyl compounds having an aralkyl or dialkyl-silyl substituent. Indene compounds substituted in the 1 position by the aralkyl or ardialkyl silyl groups are prepared by reacting omega-phenyl 1-haloalkanes or omega-phenyl-1-bromo dialkyl silyl compounds with indenyl lithium. Indene compounds substituted in the 2 position can be produced by reacting 2-indanone with omegaphenylalkyl magnesiumbromide in diethyl ether, followed by hydrolysis, followed by dehydration using p-toluene sulfonic acid.

The resulting metallocycle metallocene can be used for the polymerization. The inventive catalyst systems are particularly useful for the polymerization of alpha-olefins having 2 to 10 carbon atoms. Examples of such olefins include ethylene, propylene, butene-1, pentane-1, 3-methylbutene-1, hexene-1, 4-methylpentene-1, 3-methylpentene-1, heptene-1, octene-1, decene-1, 4,4-dimethyl-1-pentane, 4,4-diethyl-1-hexene, 3,4-dimethyl-1-hexene, and the like and mixtures thereof. The catalysts are also useful for preparing copolymers of ethylene and propylene and copolymers of ethylene or propylene and a higher molecular weight olefin. Monomers such as styrene and butadiene are also useful.

Polymerizations with the inventive catalyst can be carried out under a wide range of conditions depending upon the particular metallocene employed and the particular results desired. The inventive catalyst systems are considered useful for polymerization conducted under solution, slurry, or gas phase reaction conditions. Typically the inventive metallocene would be used with a suitable cocatalyst.

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis (pentafluorophenyl) boronate. Another example would be the use a mixture of trimethylaluminum and dimethylfluoroaluminum such as disclosed by Zambelli et, *Macromolecules*,22, 2186 (1989). In such counter anion systems the cocatalyst can be viewed as an ion-exchange compound comprising a cation which will irreversibly react with as least one ligand contained in the metallocene and a non-coordination anion which is ether a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

The currently most preferred cocatalyst is an aluminoxane. Such compounds include those compounds having repeating units of the formula

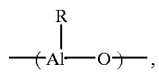

where R is generally a hydrocarbyl group having 1 to 5 carbon atoms. The organo aluminoxane component used in preparing the inventive solid catalyst system include oligomeric aluminum compounds having repeating units of the formula

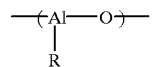

Some examples are often represented by the general formula (R—Al—O)$_n$ or R(R—Al—O—)$_n$AlR$^2$. In the general alumoxane formula R is preferably a $C_1$–$C_5$ alkyl radical, for example, methyl, ethyl, propyl, butyl or pentyl and "n" is an integer from 1 to about 50. Most preferably, R is methyl and "n" is at least 4.

Aluminoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an aluminoxane. Generally the reaction of an aluminum alkyl with a limited amount of water is postulated to yield a mixture of the linear and cyclic species of the aluminoxane. Aluminoxanes, also sometimes referred to as poly (hydrocarbyl aluminum oxides) are well known in the art and are generally prepared by reacting an hydrocarbylaluminum compound with water. Such a preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the inventive metallocene can be employed in combination with a solid organoaluminoxane which is substantially insoluble in the polymerization diluent under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640. Still another technique involves contacting a dried support such as silica with trimethyl aluminum and then adding water to form a solid containing pendant aluminoxy groups, such cocatalysts are sometimes referred to as partially hydrated trimethyl aluminum or PHT for short.

Still another technique of producing a solid cocatalyst involves contacting an organoaluminoxane with an organic borane compound free of acidic hydrogen as taught U.S. Pat. No. 5,354,721, the disclosure of which is incorporated herein by reference. Yet another technique involves contacting an organoaluminoxane with an organoboron compound having boron acid functionality, i.e. —BOH, as taught in U.S. Pat. No. 5,414,189, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in U.S. Pat. No. 5,411,925, the disclosure of which is incorporated herein by reference.

When the polymerizations are carried out in the presence of liquid diluents obviously it is important to use diluents which do not have an adverse effect upon the catalyst system. Typical liquid diluents include propane, butane, isobutane, pentane, hexane, heptane, octane, cyclohexane, methylcyclohexane, toluene, xylene, and the like. Typically the polymerization temperature can vary over a wide range, temperatures typically would be in a range of about −60° C. to about 300° C., more preferably in the range of about 20° C. to about 160° C. Typically the pressure of the polymerization would be in the range of from about 1 to about 500 atmospheres or even greater. The inventive catalyst system is particularly useful for polymerizations carried out under particle form, i.e., slurry-type polymerization conditions.

In a particularly preferred embodiment of the present invention the inventive metallocene is subjected to prepolymerization with an olefin to produce a solid catalyst system that can later be used in the polymerization of olefins. This technique is particularly useful in slurry or particle-form type polymerizations.

To prepare the solid prepolymerized catalyst system the metallocene and cocatalyst are combined in the presence of a suitable liquid to form a liquid catalyst system. It is preferred that the liquid catalyst system be prepared using an organic liquid in which the aluminoxane is at least partially soluble. The currently preferred liquids are hydrocarbons such as hexane or toluene. Typically an aromatic liquid solvent is employed. Examples include benzene, toluene, ethylbenzene, diethylbenzene, and the like. The amount of liquid to be employed is not particularly critical. Nevertheless, the amount should preferably be such as to dissolve at least a portion of the product of the reaction between the metallocene and the aluminoxane, provide desirable polymerization viscosity for the prepolymerization, and to permit good mixing. The temperature is preferably kept below that which would cause the metallocene to decompose. Typically the temperature would be in the range of −50° C. to 100° C. Preferably, the metallocene, a cocatalyst, such as an aluminoxane, and the liquid diluent are combined at room temperature, i.e. around 10 to 30° C. The reaction between the aluminoxane and the metallocene is relatively rapid. The reaction rate can vary depending upon the ligands of the metallocene. It is generally desired that they be contacted for at least about a minute to about 1 hour.

It is within the scope of the invention to form the liquid catalyst system in the presence of a particulate solid. Any number of particulate solids can be employed as the particulate solid. Typically the support can be any organic or inorganic solid that does not interfere with the desired end result. Examples include porous supports such as talc, inorganic oxides, and resinous support materials such as particulate polyolefins. Examples of inorganic oxide materials include Groups II, III, IV or V metal oxides such as silica, alumina, silica-alumina, and mixtures thereof Other examples of inorganic oxides are magnesia, titania, zirconia, and the like. Other suitable support materials which can be employed include materials such as, magnesium dichloride, and finely divided polyolefins, such as polyethylene. It is within the scope of the present invention to use a mixture of one or more of the particulate solids.

It is generally desirable for the solid to be thoroughly dehydrated prior to use, preferably it is dehydrated so as to contain less than 1% loss on ignition. Thermal dehydration treatment may be carried out in vacuum or while purging with a dry inert gas such as nitrogen at a temperature of about 20° C. to about 1000° C., and preferably, from about 300° C. to about 800° C. Pressure considerations are not critical. The duration of thermal treatment can be from about 1 to about 24 hours. However, shorter or longer times can be employed provided equilibrium is established with the surface hydroxyl groups.

Dehydration can also be accomplished by subjecting the solid to a chemical treatment in order to remove water and reduce the concentration of surface hydroxyl groups. Chemical treatment is generally capable of converting all water and hydroxyl groups in the oxide surface to relatively inert species. Useful chemical agents are for example, trimethylaluminum, ethyl magnesium chloride, chlorosilanes such as $SiCl_4$, disilazane, trimethylchlorosilane, dimethylaminotrimethylsilane and the like.

The chemical dehydration can be accomplished by slurrying the inorganic particulate material such as, for example silica, in an inert low boiling hydrocarbon, such as for example, hexane. During the chemical dehydration treatment, the silica should be maintained in a moisture and oxygen free atmosphere. To the silica slurry is then added a low boiling inert hydrocarbon solution of the chemical dehydrating agent, such as, for example dichloroldimethylsilane. The solution is added slowly to the slurry. The temperature ranges during chemical dehydration reaction can be from about 20° C. to about 120° C., however, higher and lower temperatures can be employed. Preferably, the temperature will be about 50° C. to about 100° C. The chemical dehydration procedure should be allowed to proceed until all the substantially reactive groups are removed from the particulate support material as indicated by cessation of gas evolution. Normally, the chemical dehydration reaction will be allowed to proceed from about 30 minutes to about 16 hours, preferably, 1 to 5 hours. Upon completion of the chemical dehydration, the solid particulate material may be filtered under a nitrogen atmosphere and washed one or more times with a dry, oxygen free inert solvent. The wash solvents as well as the diluents employed to form the slurry and the solution of chemical dehydrating agent, can be any suitable inert hydrocarbon. Illustrative of such hydrocarbons are pentane, heptane, hexane, toluene, isopentane and the like.

Another chemical treatment that can be used on solid inorganic oxides such as silica involves reduction by contacting the solid with carbon monoxide at an elevated temperature sufficient to convert substantially all the water and hydroxyl groups to relatively inactive species.

The specific particle size of the support or inorganic oxide, surface area, pore volume, and number of hydroxyl groups is not considered critical to its utility in the practice of this invention. However, such characteristics often determine the amount of support to be employed in preparing the catalyst compositions, as well as affecting the particle morphology of polymers formed. The characteristics of the carrier or support must therefore be taken into consideration in choosing the same for use in the particular invention.

It is also within the scope of the present invention to add such a particulate solid to the liquid catalyst system after it has been formed and to carry out the prepolymerization in the presence of that solid.

The amount of aluminoxane and metallocene used in forming the liquid catalyst system for the prepolymerization can vary over a wide range. Typically, however, the molar ratio of aluminum in the aluminoxane to transition metal of the metallocene is in the range of about 1:1 to about 20,000:1, more preferably, a molar ratio of about 50:1 to about 2000:1 is used. If a particulate solid, i.e. silica, is used generally it is used in an amount such that the weight ratio of the metallocene to the particulate solid is in the range of about 0.00001/1 to 1/1, more preferably 0.0005/1 to 0.2/1.

The prepolymerization is conducted in the liquid catalyst system, which can be a solution, a slurry, or a gel in a liquid. A wide range of olefins can be used for the prepolymerization. Typically, the prepolymerization will be conducted using an olefin, preferably selected from ethylene and non-aromatic alpha-olefins, and as propylene. It is within the scope of the invention to use a mixture of olefins, for example, ethylene and a higher alpha olefin can be used for the prepolymerization. The use of, a higher alpha olefin, such as 1-butene, with ethylene is believed to increase the amount of copolymerization occurring between the olefin monomer and the olefinically unsaturated portion of the metallocene.

The prepolymerization can be conducted under relatively mild conditions. Typically, this would involve using low pressures of the olefin and relatively low temperatures designed to prevent site decomposition resulting from high concentrations of localized heat. The prepolymerization typically occurs at temperatures in the range of about $-30°$ C. to about $+110°$ C., more preferably in the range of about $+10$ to about $+30°$ C. The amount of prepolymer can be varied but typically would be in the range of from about 1 to about 95 wt % of the resulting prepolymerized solid catalyst system, more preferably about 5 to 80 wt %. It is generally desirable to carry out the prepolymerization to at least a point where substantially all of the metallocene is in the solid rather than in the liquid since that maximizes the use of the metallocene.

After the prepolymerization, the resulting solid prepolymerized catalyst is preferably separated from the liquid of the reaction mixture. Various techniques known in the art can be used for carrying out this step. For example, the material could be separated by filtration, decantation, or by vacuum evaporation. It is currently preferred, however, not to rely upon vacuum evaporation since it is considered desirable to remove substantially all of the soluble components in the liquid reaction product of the prepolymerization from the resulting solid prepolymerized catalyst before it is stored or used for subsequent polymerization. After separating the solid from the liquid, the resulting solid is preferably washed with a hydrocarbon and then dried using high vacuum to remove substantially all the liquids and other volatile components that might still be associated with the solid. The vacuum drying is preferably carried out under relatively mild conditions, i.e. temperatures below 100° C. More typically the prepolymerized solid is dried by subjection to a high vacuum at a temperature of about 30° C. until a substantially constant weight is achieved. A preferred technique employs at least one initial wash with an aromatic hydrocarbon, such as toluene, followed by a wash with a paraffinic hydrocarbon, such as hexane, and then vacuum drying.

It is within the scope of the present invention to contact the prepolymerization reaction mixture product with a liquid in which the prepolymer is sparingly soluble, i.e. a counter solvent for the prepolymer, to help cause soluble prepolymer to precipitate from the solution. Such a liquid is also useful for the subsequent washing of the prepolymerized solid.

It is also within the scope of the present invention to add a particulate solid of the type aforementioned after the prepolymerization. Thus one can add the solid to the liquid prepolymerization product before the counter solvent is added. In this manner soluble prepolymer tends to precipitate onto the surface of the solid to aid in the recovery of the filtrate in a particulate form and to prevent agglomeration during drying. The liquid mixture resulting from the prepolymerization or the inventive solid prepolymerized catalyst can be subjected to sonification to help break up particles if desired.

Further, if desired the recovered solid prepolymerized catalyst system can be screened to give particles having sizes that meet the particular needs for a particular type of polymerization.

Another option is to combine the recovered inventive solid prepolymerized catalyst system with an inert hydrocarbon, such as one of the type used as a wash liquid, and then to remove that liquid using a vacuum. In such a process it is sometimes desirable to subject the resulting mixture to sonification before stripping off the liquid.

The solid prepolymerized catalyst system is suitable for use in the polymerization of olefinically unsaturated monomers. Such polymerizations can be carried out under gas phase, solution phase, or slurry phase conditions. The conditions used are as conventional. One difference is that generally it is not necessary to employ an additional cocatalyst with the solid prepolymerized catalyst.

In some cases it may be found desirable to employ small amounts of an organoaluminum compound as a scavenger for poisons. The term organoaluminum compounds include compounds such as triethylaluminum, trimethylaluminum, diethylaluminum chloride, ethylaluminum dichloride, ethylaluminum sesquichloride, and the like. Trialkylaluminum compounds are currently preferred. Also in some applications it may be desirable to employ small amounts of antistatic agents which assist in preventing the agglomeration of polymer particles during polymerization. Still further, when the inventive catalyst system is added to a reactor as a slurry in a liquid, it is sometimes desirable to add a particulate dried solid as a flow aid for the slurry. Preferably the solid has been dried using one of the methods described earlier. Inorganic oxides such as silica are particularly preferred. Currently, it is preferred to use a fumed silica such as that sold under the trade name Cab-o-sil. Generally the fumed silica is dried using heat and trimethylaluminum.

The polymers produced with the catalysts herein disclosed have a wide range of uses that will be apparent to those skilled in the art from the physical properties of the respective polymers. Applications such as molding, films, adhesives, and the like are indicated.

A further understanding of the present invention and its objects and advantages will be provided by the following examples.

EXAMPLE 1

Homopolymerizations of ethylene were conducted using different unbridged bis(omega-phenylalkyl or dialkyl silyl substituted cyclopentadienyl) zirconium dichlorides. The compounds differed in the length of the group separating the phenyl and the cyclopentadienyl. The groups separating the phenyl and the cyclopentadienyl were methylene, ethylene, propylene, isopropylidene, and dimethyl silylene. In addition metallocycle metallocene of each of those compounds were prepared and evaluated as polymerization catalysts under the same conditions.

The polymerizations were carried out by combining the metallocene with a 30 weight percent toluene solution of methylaluminoxane to form a mixture in which the mole ration of the Zr of the metallocene to the Al of the aluminoxane was about 1:3000. The polymerizations were conducted in a one liter autoclave reactor in which the catalyst solution was mixed with 500 ml of n-pentane. An ethylene pressure of 10 bar was applied after the reactor reached 50° C. and the mixture was stirred for one hour with the autoclave at a temperature of about 60° C. Then the reactor was vented and the polymer recovered. The results are summarized in the following table wherein the differences in group separating the cyclopentadienyl and the phenyl are noted. The A denotes the starting metallocene and the B denotes the metallocycle produced from it. The number bracketed refers to the metallocycle metallocene of FIGS. 1–3.

TABLE 1

| Separating Group | Activity (kg polyethylene/g Zr per hour) |
|---|---|
| A. Methylidene | 140 |
| B. Methylidene (152) | 790 |
| A. Ethylidene | 336 |
| B. Ethylidene (153) | 1810 |
| A. Propylidene | 1506 |
| B. Propylidene (154) | 5577 |
| A. Isopropylidene | 6 |
| B. Isopropylidene (159) | 8 |
| A. Dimethylsilylene | 129 |
| B. Dimethylsilylene (159) | 164 |

The results show that the metallocycles were more active in all cases. The results also show that the activity increased as the length of the separating group increased. The isopropylidene group produced much less active catalysts than the methylidene group. The straight chain 3 carbon propylidene group provided the most active catalyst.

EXAMPLE 2

Another series of unbridged bis(omega aryl methylidene cyclopentadienyl) metallocenes were produced in which the nature of the aryl group differed and then the metallocycles were prepared from those metallocenes. All were then evaluated for the polymerization of ethylene as described above. The results are summarized in the following table, wherein again the A refers the starting metallocene and the B refers to the corresponding metallocycle.

TABLE 2

| Aromatic Group | Activity (kg polyethylene/g Zr per hour) |
|---|---|
| A. Phenyl | 140 |
| B. Phenyl (152) | 790 |
| A. 4-methylphenyl | 1881 |
| B. 4-methylphenyl (155) | 1231 |
| A. Naphthyl | 1020 |
| B. Naphthyl (158) | 1413 |
| A. 3,5-dimethylphenyl | 1120 |
| B. 3,5-dimethylphenyl (157) | 1040 |

The results show that increasing the number of carbon atoms in the aryl group increased the activity for both the metallocene dichlorides and the metallocycles; however, in this case the metallocycles having methyl substituents on the phenyl group were not as active as the metallocene dichlorides from which they were made.

EXAMPLE 3

Another series of unbridged metallocene dichlorides were produced but in this case only one of the cyclodienyl groups, namely cyclopentadienyl, was substituted with an omega arylalkyl substituent. The other cyclodienyl group was indenyl. Metallocycles were produced from those metallocenes and all the metallocenes evaluated for the polymerization of ethylene as described above. The results are summarized in the following table.

TABLE 3

| Separating Group | Activity (kg polyethylene/g Zr per hour) |
| --- | --- |
| A. Methylene | 2887 |
| B. Methylene (160) | 2850 |
| A. Ethylene | 1899 |
| B. Ethylene (161) | 2460 |
| A. Propylene | 3534 |
| B. Propylene (162) | 4560 |

These polymers had higher molecular weights that the polymers produced using symmetrically substituted bis(aralkyl cyclodienyl) metallocenes. With the exception of the metallocycle having the propylene, i.e propylidiene, group these metallocenes were more active that the symmetrically substituted bis(aralkyl cyclodienyl) metallocenes of Table 1

That which is claimed is:

1. A catalyst composition useful for the polymerization of olefins comprising a composition resulting from the combination of a metallocycle metallocene and a suitable organometallic cocatalyst, said metallocycle metallocene being prepared by reacting a first metallocene having an aralkyl group, an aryl alkyldialkylsilyl group, or an aryl dialkyl silyl group attached to a cyclodienyl group with about two molar equivalents of an alkali metal alkyl having at least 4 carbon atoms.

2. A composition according to claim 1 wherein the metallocene that is reacted with the two molar equivalents of the alkali metal alkyl is selected from the group consisting of bis(benzyl cyclupentadienyl) zirconium dichloride, bis (phenyl ethylidene cyclopentadienyl) zirconium dichloride, bis(phenyl n-propylidene cyclopentadienyl) zirconium dichloride, bis(methyl benzyl cyclopentadienyl) zirconium dichloride, bis(dimethyl benzyl cyclopentadienyl) zirconium dichloride, bis(naphthyl methylene cyclopentadienyl) zirconium dichloride, bis(phenyl dimethylsilyl cyclopentadienyl) zirconium dichloride, (benzyl cyclopentadienyl) (indenyl) zirconium dichloride, (phenyl ethylidene cyclopentadienyl) (indenyl) zirconium dichloride, (phenyl n-propylidene cyclopentadienyl) (indenyl) zirconium dichloride, (phenyl isopropylidene cyclopentadienyl) (indenyl) zirconium dichloride, (benzyl methylcyclopentadienyl) (indenyl) zirconium dichloride, bis (phenyl isopropylidene cyclopentadienyl) zirconium dichloride, bis(phenyl n-propylidene indenyl) zirconium dichloride, bis(phenyl dimethylsilyl indenyl) zirconium dichloride, (benzyl indenyl) (indenyl) zirconium dichlorde, (phenyl ethylidene indenyl) (indenyl) zirconium dichloride, (phenyl dimethylsilyl indenyl) (indenyl) zirconium dichloride, bis(cyclopentadienyl isopropylidene indenyl) zirconium dichloride, bis(phenyl ethylidene indenyl) zirconium dichloride, (benzyl indenyl) (fluorenyl) zirconium dichloride, and bis(benzyl indenyl) zirconium dichloride.

3. A composition according to clam 1 wherein the starting metallocene is an unbridged metallocene in which one of the cyclopentadienyl groups is indenyl and the other cyclopentadienyl group is an omega aryl alkyl-substituted cyclopentadienyl.

4. A catalyst composition according to claim 1 wherein the cocatalyst comprises an alkylaluminoxane.

5. A catalyst composition according to claim 1 which is a solid produced by prepolymerizing an olefin in the presence of the metallocycle metallocene and the alkylaluminoxane.

6. A catalyst composition according to claim 4 wherein the metallocene has the formula

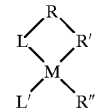

wherein L is a radical having a cyclodienyl skeleton selected from hydrocarbyl substituted and unsubstituted cyclopentadienyl, indenyl, fluorenyl, and tetrahydroindenyl; R' is an aryl group; R is a divalent alkyl or dialkylsilyl radical wherein the number of atoms separating L and R' is in the range of 1 to 3, L' is a hydrocarbyl substituted and unsubstituted radical having a cyclopentadienyl skeleton selected from the group consisting of cyclopentadienyl, indenyl, fluorenyl, and tetrahydroindenyl; R" is an aliphatic radical having 1 to 10 carbon atoms; and M selected from Zr, Hf, or Ti, L and L" optionally being connected to each other by a bridging structure.

7. A catalyst composition useful for the polymerization of olefins comprising a composition resulting from the combination of a metallocycle metallocene and an alkylaluminoxane, said metallocycle metallocene having the formula

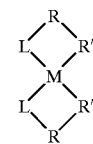

wherein L is a cyclopentadienyl radical, each R can be the same or different and is selected from the group consisting of divalent alkyl or dialkylsilyl radicals wherein the number of atoms separating L and R' is in the range of 1 to 3, and one R' is an indenyl radical and the other is an indanyl radical.

* * * * *